(12) United States Patent
Martin

(10) Patent No.: US 11,026,577 B2
(45) Date of Patent: Jun. 8, 2021

(54) REBOUND TONOMETRY METHOD AND APPARATUS

(71) Applicant: Reichert, Inc., Depew, NY (US)

(72) Inventor: Gabriel N. Martin, Buenos Aires (AR)

(73) Assignee: Reichert, Inc., Depew, NY (US)

(*) Notice: Subject to any disclaimer, the term of this patent is extended or adjusted under 35 U.S.C. 154(b) by 313 days.

(21) Appl. No.: 16/007,501

(22) Filed: Jun. 13, 2018

(65) Prior Publication Data

US 2019/0380577 A1   Dec. 19, 2019

(51) Int. Cl.
*A61B 3/16* (2006.01)
*A61B 3/00* (2006.01)

(52) U.S. Cl.
CPC ............. *A61B 3/16* (2013.01); *A61B 3/0025* (2013.01)

(58) Field of Classification Search
CPC ............ A61B 3/16; A61B 3/0025; A61B 3/10
See application file for complete search history.

(56) References Cited

U.S. PATENT DOCUMENTS

| | | | | |
|---|---|---|---|---|
| 3,992,926 | A  * | 11/1976 | Berryhill | A61B 3/16 600/405 |
| 6,093,147 | A  * | 7/2000 | Kontiola | A61B 3/16 600/405 |
| 6,817,981 | B2 | 11/2004 | Luce | |
| 6,875,175 | B2 | 4/2005 | Luce | |
| 7,004,902 | B2 | 2/2006 | Luce | |
| 7,481,767 | B2 | 1/2009 | Luce | |
| 8,551,013 | B2 | 10/2013 | Steinmueller | |
| 8,551,014 | B2 | 10/2013 | Koest et al. | |
| 8,556,823 | B2 | 10/2013 | Koest et al. | |
| 8,939,907 | B2 * | 1/2015 | Koest | A61B 3/165 600/401 |
| 2004/0183998 | A1 * | 9/2004 | Luce | A61B 3/165 351/212 |
| 2005/0137473 | A1 | 6/2005 | Kontiola | |
| 2008/0103381 | A1 | 5/2008 | Kontiola | |

FOREIGN PATENT DOCUMENTS

| | | |
|---|---|---|
| CN | 101773381 A | 7/2010 |
| CN | 104274153 B | 2/2016 |
| DE | 102006037767 A1 | 2/2008 |
| EP | 1545294 B1 | 2/2008 |
| WO | 2014074157 A1 | 5/2014 |
| WO | 2017103330 A1 | 6/2017 |

\* cited by examiner

*Primary Examiner* — Devin B Henson
*Assistant Examiner* — Joseph A Tombers
(74) *Attorney, Agent, or Firm* — Hodgson Russ LLP

(57) ABSTRACT

Viscoelastic properties of the cornea are derived from an ophthalmic measurement signal representing velocity as a function of time of a contact probe rebounded by the eye. The viscoelastic properties include a "Lost Energy Ratio" (LER), a "Time Shift" (TS), a damping parameter ($\sigma$), and an elastic parameter ($\eta$). An improved method for determining intra-ocular pressure from the measurement signal is also disclosed, wherein a first derivative of the measurement signal at a moment in time when velocity of the probe is zero due to contact of the probe with the cornea is calculated and correlated to an intra-ocular pressure value.

20 Claims, 2 Drawing Sheets

REBOUND TONOMETRY METHOD AND APPARATUS

FIELD OF THE INVENTION

The present invention relates to rebound tonometers for measuring intraocular pressure (IOP).

A rebound tonometer is a hand-held instrument that propels a movable measurement probe in a controlled manner toward the cornea of an eye to measure intraocular pressure. During a measurement, the probe contacts the cornea, is decelerated at a rate which depends on intraocular pressure, and then rebounds in a direction away from the cornea back toward the instrument housing. The rebound tonometer detects the motion of the measurement probe and determines intraocular pressure based on the detected motion of the probe. For example, the measurement probe may have a magnetized shaft that travels within a coil in the instrument housing. The coil may be energized momentarily to propel the probe toward the cornea by electromagnetic force, and then, after energizing current to the coil is shut off, a current may be induced in the coil by the moving probe to provide a detectable voltage signal representing velocity of the probe as a function of time. The voltage signal may be recorded and processed to determine a measured IOP value. FIG. 2 shows a typical voltage signal generated during a rebound tonometer measurement.

It has been demonstrated that the rate of change of the velocity of the probe caused by the eye is indicative of the IOP. Greater deceleration of the probe correlates to a higher IOP, and vice versa. By calculating a slope of the voltage signal from the time the probe makes contact with the cornea ($t_{in}$ in FIG. 2) until the time the probe is rebounded away from contact with the cornea ($t_{out}$ in FIG. 2), an average deceleration of the probe is determined and is correlated to a measured value of IOP. For example, the voltage signal from $t_{in}$ to $t_{out}$ may be fitted to a line, and the slope of the line may be calculated. A drawback of this approach is that during the analyzed time period, viscoelastic forces attributed to biomechanical properties of the corneal tissue are acting on the probe and will influence the average deceleration of the probe. Consequently, a first test subject having the same true IOP as a second test subject but a stiffer cornea than the second test subject will record a higher IOP measurement value than the second test subject.

The rebound tonometry process described above analyzes the voltage signal solely to derive IOP. No other useful information is derived from the measured voltage signal.

In the realm of non-contact tonometry in which an air pulse is used to reversibly deform the cornea, it is known to evaluate a pressure differential between two momentary corneal applanation events to derive biomechanical characteristics of the cornea. As the air pulse forces the cornea inward from its normal convex shape, a central area of the cornea becomes flattened (applanated) momentarily as the cornea transitions from convex to concave. When the air pulse dissipates, the cornea returns in an outward direction from concave back to convex, once again passing through a momentary state of applanation. The inward and outward applanation events are observable as signal peaks in an optoelectronic monitoring system, and respective air pulse pressures corresponding to the inward and outward applanation events are detected. The pressure differential between the instantaneous inward and outward applanation events is referred to as "corneal hysteresis." Observation and measurement of corneal hysteresis has led to improvements in the accuracy of the intraocular pressure measurement and derivation of supplemental information about biomechanical characteristics of the corneal tissue. In this regard, see U.S. Pat. Nos. 6,817,981; 6,875,175; 7,004,902; 7,481,767 and 7,798,962. For example, the OCULAR RESPONSE ANALYZER® ophthalmic instrument available from Reichert, Inc., assignee of the present application, measures corneal hysteresis as a predictor of glaucoma progression.

While corneal hysteresis measured by a non-contact procedure is an important and useful improvement in ophthalmic testing, it is based on two "snapshots" of the corneal deformation process corresponding to the momentary inward and outward applanation events. The vast majority of the corneal deformation process, i.e. corneal deformation occurring before, between, and after the inward and outward applanation events, is ignored.

SUMMARY OF THE INVENTION

The inventor has recognized that useful information other than IOP may be extracted from the measured voltage signal obtained during a rebound tonometer measurement. More specifically, viscoelastic properties of the cornea may be derived from the measurement signal representing velocity as a function of time of a contact probe rebounded by the eye.

A "Lost Energy Ratio" (LER) is one parameter which may be calculated from the measured voltage signal. The LER is proportional to the kinetic energy of the probe lost during the measurement process due to viscous damping by the cornea. The LER must be zero in a perfectly elastic system lacking friction or any other damping mechanism.

Another important parameter that can be calculated is a "Time Shift" (TS), which is defined as a time interval between the moment when velocity of the probe is zero and the moment when force applied on the probe by the cornea (or the probe deceleration) is at a maximum. If the system is purely elastic, then TS is equal to zero, otherwise TS is greater than zero.

Both LER and TS may be calculated from the velocity signal without any assumption about the equation that governs motion of the probe during the measurement. Further parameters may be extracted from the velocity signal if assumptions are made about non-conservative (i.e. viscous) forces acting on the probe. For example, a damping parameter ($\sigma$) and an elastic parameter ($\eta$) of the system may be determined as further parameters.

The parameters summarized above may be used to assess other ophthalmic conditions beyond IOP. For example, LER indicates a capacity of the cornea to absorb energy, a property found to a greater degree in healthy corneas. As another example, the damping parameter $\sigma$ correlates with corneal hysteresis mentioned above, which is a predictor of glaucoma progression.

The inventor has also recognized that an IOP measurement value which is less susceptible to measurement error caused by viscous forces associated with the cornea is achievable by taking a first derivative of the measured voltage signal at the moment when the net viscous corneal forces acting on the probe are zero, i.e. when the velocity of the probe is zero due to contact of the probe with the cornea, and correlating the first derivative to an IOP value.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
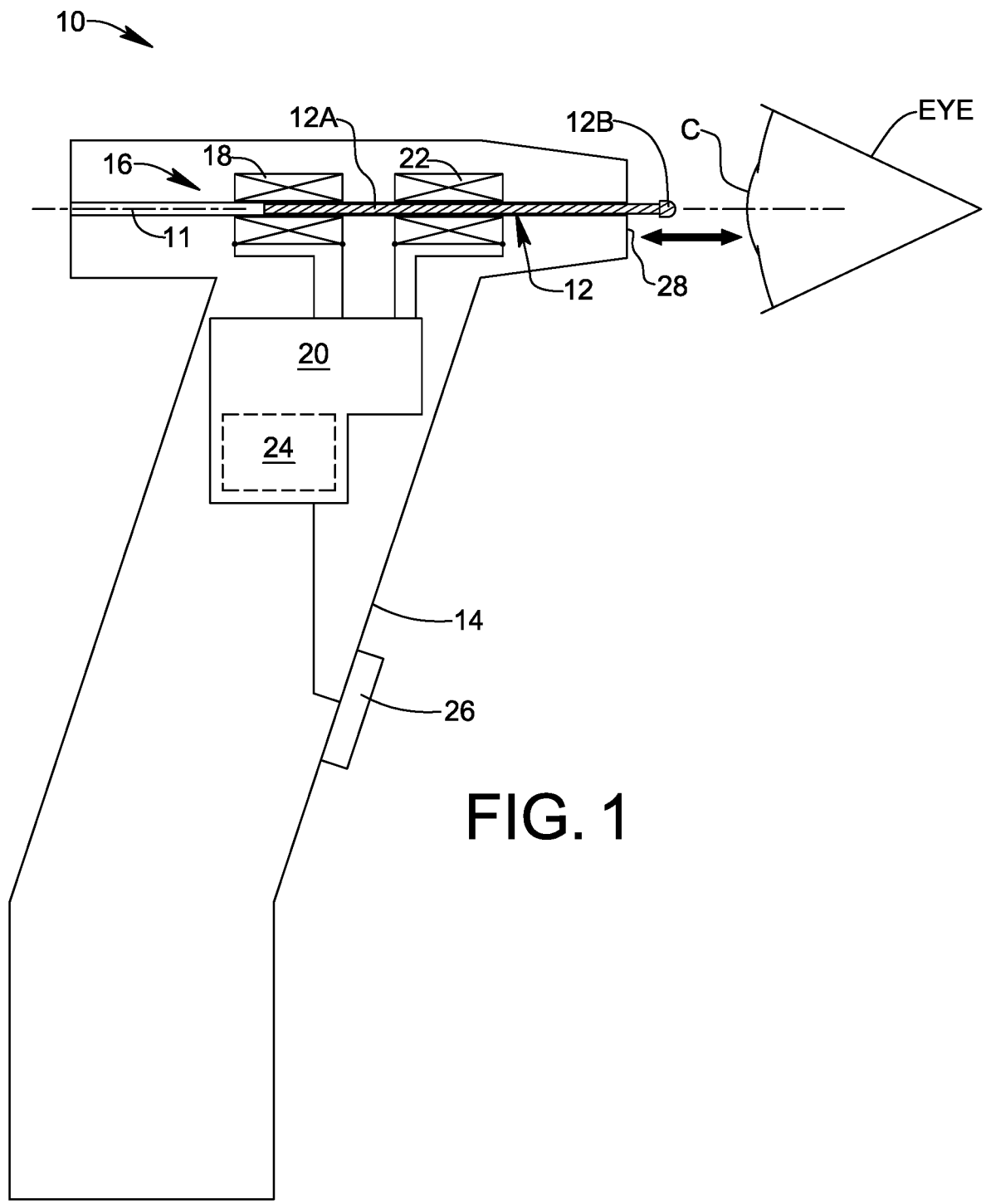
FIG. 1 is a schematic view of an ophthalmic instrument formed in accordance with an embodiment of the present invention.

FIG. 1 is a schematic view showing an ophthalmic instrument 10 formed in accordance with an embodiment of the present invention. Ophthalmic instrument 10 generally comprises a disposable probe 12 and a hand-held housing 14 containing a measurement system 16 configured to propel probe 12 in a forward direction toward an eye of test subject, wherein probe 12 contacts a cornea C of the eye and is rebounded from the cornea in a reverse direction opposite the forward direction. Measurement system 16 is further configured to provide a measurement signal representing velocity of probe 12 as a function of time.

Probe 12 may include an elongated shaft 12A, at least a portion of which is made of a magnetic material, and a rounded tip 12B at an end of shaft 12A for contacting cornea C. Measurement system 16 may include a conductive drive coil 18 in which probe 12 is received, and a controller 20 configured to momentarily energize drive coil 18 to propel probe 12 forward toward the eye by electromagnetic force. Measurement system 16 may include a conductive measurement coil 22 through which probe 12 moves, and controller 20 may be further configured to measure a current induced in measurement coil 22 by the moving probe 12 and provide a measurement signal representing velocity of the probe as a function of time. The embodiment depicted in FIG. 1 shows drive coil 18 and measurement coil 22 as being two different conductive coils. Alternatively, a single coil may act sequentially during a measurement cycle as both the drive coil and the measurement coil, thus eliminating the need for a second coil.

As known in the art of rebound tonometers, instrument 10 may further comprise an opto-electronic alignment detection system (not shown) and a display (not shown) to guide and confirm alignment of a measurement axis 11 of instrument 10 with cornea C and positioning of a front nose 28 of instrument 10 at a predetermined working distance from cornea C. A trigger button 26 may be provided on housing 14 for enabling a user to send a signal to controller 20 to initiate a measurement, and/or the alignment detection system may automatically send a signal to controller 20 to initiate a measurement when alignment and proper working distance are confirmed by the alignment detection system.

Measurement system 16 may further include signal processing logic 24 configured to calculate at least one viscoelastic parameter of the eye based on the measurement signal. The measurement signal generated by measurement coil 22 may be in the form of an analog voltage signal. Signal processing logic 24 may be configured to convert the analog voltage signal to digital form, and to compute one or more viscoelastic parameters of the eye from the digitized measurement signal. For example, signal processing logic 24 may comprise an analog-to-digital signal converter and a programmed microprocessor for executing instructions stored in memory for calculating at least one viscoelastic parameter. Signal processing logic 24 may also be configured to calculate IOP based on the measurement signal.

A first viscoelastic parameter of the eye which may be computed by signal processing logic 24 is referred to herein as a "Lost Energy Ratio" (LER). The LER is proportional to the kinetic energy of probe 12 lost during the measurement process due to viscous damping by cornea C. The LER by definition must be zero in a perfectly elastic system lacking friction or any other damping mechanism by which kinetic energy is lost.

Figure 2:
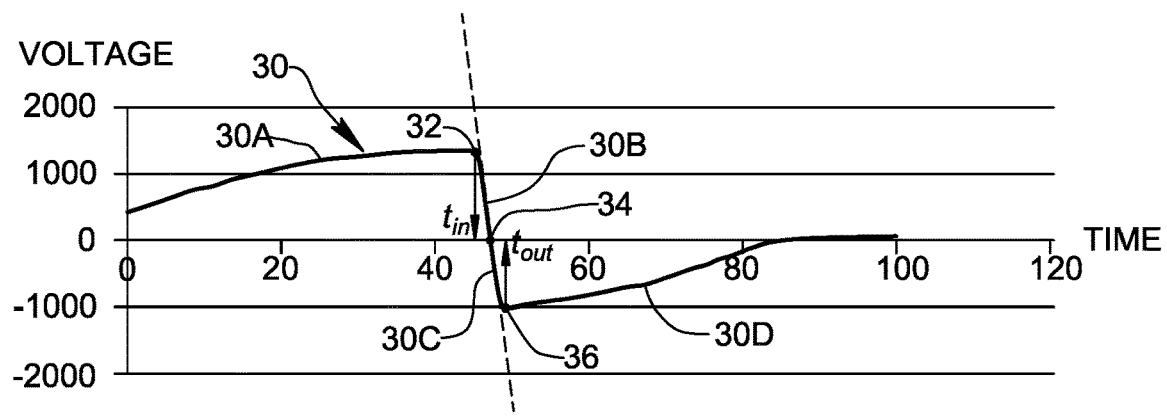
FIG. 2 is a graph representing velocity of a measurement probe of the ophthalmic instrument as a function of time during a measurement cycle in which the probe is propelled into contact with an eye and rebounded from the eye.

LER may be understood by reference to FIG. 2, which is a graph of a typical measurement signal 30 representing the velocity of measurement probe 12 as a function of time during a measurement cycle in which the probe is propelled forward from an original firing position and makes contact with cornea C, and is rebounded from the cornea in an opposite or reverse direction. A first portion 30A of measurement signal 30 illustrates that probe 12 accelerates or increases in velocity until it reaches a substantially constant velocity. At point 32, the probe tip 12B makes contact with cornea C. A second portion 30B of measurement signal 30 exhibits a sharp downward slope corresponding to rapid deceleration of probe 12 until the probe reaches zero velocity at point 34. At point 34, probe 12 starts to travel in the opposite or reverse direction. In a third portion 30C of measurement signal 30, probe 12 undergoes rapid acceleration in the reverse direction until point 36, when the probe loses contact with cornea C. Finally, in a fourth portion 30D of measurement signal 30, probe 12 decelerates until it comes to a stop in its original firing position.

It can be shown that the kinetic energy of probe 12 lost during the measurement process due to viscous damping by cornea C is proportional to the kinetic energy difference between point 32 and point 36, divided by the initial kinetic energy at point 32. Thus, LER is defined by $$LER = \frac{K_{in} - K_{out}}{K_{in}}$$

wherein $K_{in}$ is the kinetic energy at time $t_{in}$ at which the probe tip 12B makes contact with cornea C as the probe travels in the forward direction, and $K_{out}$ is the kinetic energy at time $t_{out}$ at which the probe tip 12B loses contact with cornea C as the probe travels in the reverse direction. $K_{in}$ and $K_{out}$ may be computed from $$K_{in} = \tfrac{1}{2}mV_{in}^2 \text{ and } K_{out} = \tfrac{1}{2}mV_{out}^2$$

wherein m is the mass of probe 12, $V_{in}$ is the velocity of probe 12 at time $t_{in}$, and $V_{out}$ is the velocity of probe 12 at time $t_{out}$. Thus, calculation of LER from measurement signal 30 reduces to $$LER = \frac{V_{in}^2 - V_{out}^2}{V_{in}^2}$$

Figure 3:
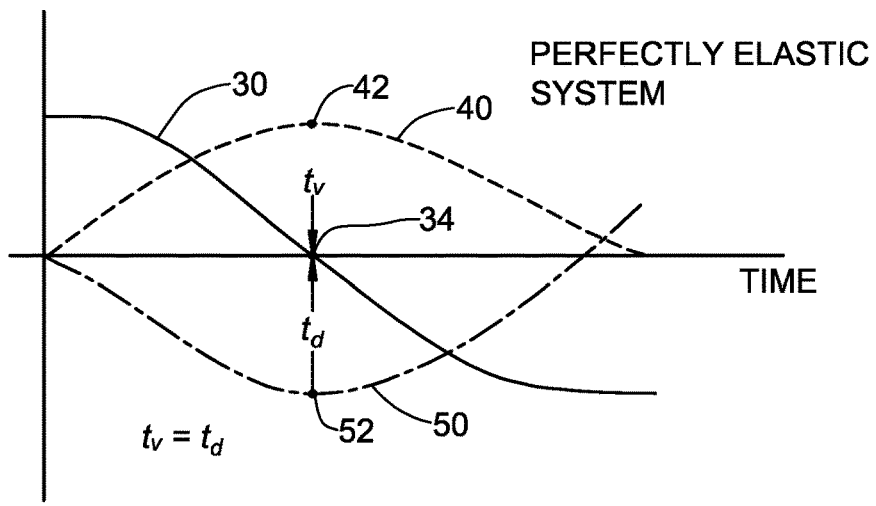
FIG. 3 is a graph illustrating probe displacement, velocity, and deceleration as a function of time during a measurement cycle assuming a perfectly elastic eye system.
Figure 4:
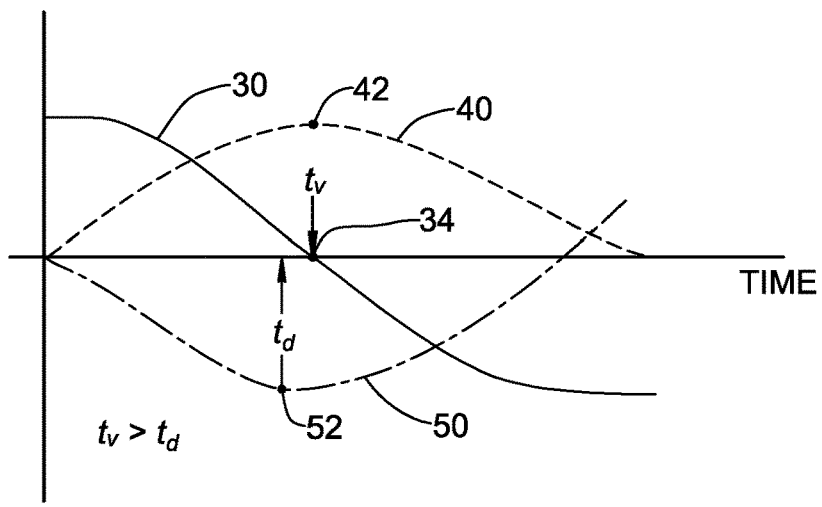
FIG. 4 is a graph similar to that of FIG. 3, wherein the eye system is not perfectly elastic and some viscous damping occurs.

A second viscoelastic parameter of the eye which may be computed from measurement signal 30 by signal processing logic 24 is referred to herein as a "Time Shift" (TS). Reference is made to FIGS. 2-4 to describe the TS parameter. In FIGS. 3 and 4, a portion of the probe velocity measurement signal 30 is plotted together with a probe displacement curve 40 and a probe deceleration curve 50 which represent probe displacement and probe deceleration as a function of time, respectively. As will be understood, probe displacement curve 40 is the integral of probe velocity measurement signal 30 over time, and probe deceleration curve 50 is the additive inverse of the first derivative of measurement signal 30 with respect to time. FIG. 3 illustrates a theoretical perfectly elastic eye system, whereas FIG. 4 illustrates a real eye system which is not perfectly elastic and in which some viscous damping occurs.

TS is defined as a difference in time between the moment $t_v$ when velocity of probe 12 is equal to zero (point 34 on measurement signal 30) and the moment $t_d$ when force applied on probe 12 by cornea C (or probe deceleration) is maximum (point 52 on deceleration curve 50). Thus, TS is given by $$TS = t_v - t_d$$

If the eye system is purely elastic, as in FIG. 3, then $t_v$ equals $t_d$ and TS equals zero. Otherwise, as shown in FIG. 4, there is some viscous damping, and TS is greater than zero. In both FIGS. 3 and 4, the time at which maximum displacement 42 is reached by probe 12 is the same as the time $t_v$ when the probe has zero velocity due to deceleration by the eye.

Both parameters LER and TS described above can be calculated from measurement signal 30 without any assumption about the equation of motion that governs probe 12 during the measurement rebound process.

A third viscoelastic parameter of the eye computable by signal processing logic 24 from measurement signal 30 is a damping parameter $\sigma$ which correlates with hysteresis of the cornea. Damping parameter $\sigma$ is expressed by $$\sigma = -\frac{K_{in} - K_{out}}{\oint \left(\frac{dx}{dt}\right)^2 dt}$$

where x is the displacement of probe 12, and dx/dt is the instantaneous velocity of probe 12. Damping parameter $\sigma$ is zero for purely conservative (i.e. perfectly elastic) systems, and is greater than zero for viscoelastic systems such as an eye.

A fourth viscoelastic parameter of the eye computable by signal processing logic 24 from measurement signal 30 is an elastic parameter $\eta$ describing elastic force of the system. If it is assumed that the entire equation of motion governing probe 12 is $$m\frac{d^2x}{dt^2} = -\sigma\frac{dx}{dt} - \eta x \qquad \text{Equation \#1}$$

where m is the mass of probe 12, then elastic parameter $\eta$ may be calculated by solving Equation #1 and further assuming that $4m\eta - \sigma^2 > 0$. A value $\alpha$ may be calculated numerically from $$\sigma \text{Tan}[\alpha t_v] - 2m\alpha = 0$$
$$\sigma \frac{\text{Tan}[\alpha t_v]}{\alpha t_v} - \frac{2m}{t_v} = 0$$

where $t_v$ is the time when probe velocity is zero and $$\alpha \equiv \frac{\sqrt{4m\eta - \sigma^2}}{2m}.$$

Finally, it is possible to calculate elastic parameter $\eta$ as follows:

$$\eta = \frac{(2m\alpha)^2 + \sigma^2}{4m}. \qquad \text{Equation \#2}$$

It has been observed that the elastic parameter $\eta$ correlates strongly with IOP for one given eye and is independent of damping forces.

It has been well understood for decades that IOP is the leading screening metric for glaucoma. In more recent years, understanding the biomechanical properties of the cornea has also been shown to be very helpful in predicating glaucoma progression. One example is that corneas having lower elasticity and higher viscous damping capability have been shown to be at lower relative risk for glaucoma progression. Conversely, corneas exhibiting greater elasticity and lower viscous damping capability have been shown to be at higher relative risk for glaucoma progression. An ophthalmic instrument and method for measuring the viscoelastic parameters disclosed herein provides information in addition to IOP that is useful for assessing a likelihood of glaucoma progression. The additional information may also allow for more accurate IOP measurements to be made by compensating or otherwise adjusting IOP measurements to take into account properties of the eye system that influence the measured IOP. Signal processing logic 24 may be configured with executable software instructions to make such adjustments of the measured IOP automatically before an IOP value is reported to the user. The additional information embodied by the calculated viscoelastic parameters may also be used as a screening tool to reduce complications in refractive surgery, and to improve detection and treatment of corneal dystrophies.

Signal processing logic 24 may also be configured with executable software instructions to calculate a first derivative of the measurement signal at the moment in time $t_v$ when velocity of probe 12 is zero due to contact of probe 12 with cornea C, and to correlate the first derivative to an IOP value. This approach differs from and is advantageous over known schemes wherein a portion of measurement signal 30 from $t_{in}$ to $t_{out}$ is fitted to a line, and the slope of the line is calculated. At time $t_v$, the net viscous corneal forces acting on probe 12 are zero. Consequently, the present technique is less susceptible to measurement error caused by viscous forces associated with the cornea than the line fitting technique of the prior art.

In the above embodiments, measurement signal 30 is generated by measurement coil 22 as a result of current induced in measurement coil 22 by the moving probe 12.

Those skilled in the art will recognize that other means for generating a measurement signal representing velocity of the probe as a function of time are possible. For example, such a measurement signal may be generated by capturing and analyzing a series of images showing the journey of probe 12 to and from the eye. A camera separate from or integral with ophthalmic instrument 10 may be used to record images representing movement of probe, and the images may be processed to provide a measurement signal representing velocity of the probe as a function of time.

The described parameters and IOP value calculated by signal processing logic 24 may be stored in a memory and/or reported to a display, wherein the memory and display may be integral with ophthalmic instrument 10, or connected in wired or wireless communication with ophthalmic instrument 10.

While the invention has been described in connection with exemplary embodiments, the detailed description is not intended to limit the scope of the invention to the particular forms set forth. The invention is intended to cover such alternatives, modifications and equivalents of the described embodiment as may be included within the scope of the claims.

What is claimed is:

1. An ophthalmic instrument comprising:
a probe;
a conductive drive coil in which the probe is received;
a controller configured to momentarily energize the drive coil to propel the probe in a forward direction toward an eye of test subject, wherein the probe contacts a cornea of the eye and is rebounded from the cornea in a reverse direction opposite the forward direction;
a conductive measurement coil through which the probe moves;
wherein the controller is further configured to measure a current induced in the measurement coil by the moving probe and provide a measurement signal representing velocity of the probe as a function of time, and wherein the drive coil is energized such that a magnitude of the velocity of the probe is not kept constant after the probe is rebounded from the cornea; and
signal processing logic configured to calculate at least one viscoelastic parameter of the cornea based on the measurement signal.

2. The ophthalmic instrument according to claim 1, wherein the signal processing logic is further configured to calculate an intra-ocular pressure value based on the measurement signal.

3. The ophthalmic instrument according to claim 2, wherein the signal processing logic is configured to calculate a first derivative of the measurement signal at a moment in time when velocity of the probe is zero due to contact of the probe with the cornea, and the intra-ocular pressure value is a correlate of the first derivative.

4. The ophthalmic instrument according to claim 2, wherein the signal processing logic is further configured to adjust the intra-ocular pressure value based on the at least one viscoelastic parameter.

5. The ophthalmic instrument according to claim 1, wherein the at least one viscoelastic parameter includes at least one parameter selected from the group of parameters consisting of: a Lost Energy Ratio, a Time Shift, a damping parameter, and an elastic parameter.

6. The ophthalmic instrument according to claim 1, wherein the drive coil is the measurement coil.

7. The ophthalmic instrument according to claim 1, wherein the drive coil and the measurement coil are different conductive coils.

8. An ophthalmic measurement method comprising:
propelling a probe in a forward direction toward an eye of a test subject, wherein the probe contacts a cornea of the eye and is rebounded from the cornea in a reverse direction opposite the forward direction;
detecting a measurement signal representing velocity of the probe as a function of time, wherein the probe is propelled such that a magnitude of the velocity of the probe is not kept constant after the probe is rebounded from the cornea; and
calculating at least one viscoelastic parameter of the eye cornea based on the measurement signal.

9. The ophthalmic measurement method according to claim 8, further comprising calculating an intra-ocular pressure value based on the measurement signal.

10. The ophthalmic measurement method according to claim 9, wherein the intra-ocular pressure value is calculated by calculating a first derivative of the measurement signal at a moment in time when velocity of the probe is zero due to contact of the probe with the cornea, and correlating the first derivative to intra-ocular pressure.

11. The ophthalmic measurement method according to claim 9, further comprising adjusting the intra-ocular pressure value based on the at least one viscoelastic parameter.

12. The ophthalmic instrument according to claim 8, wherein the at least one viscoelastic parameter includes at least one parameter selected from the group of parameters consisting of: a Lost Energy Ratio, a Time Shift, a damping parameter, and an elastic parameter.

13. The ophthalmic measurement method according to claim 8, wherein the measurement signal is detected using a measurement coil through which the probe moves, whereby the moving probe induces a current in the measurement coil.

14. The ophthalmic measurement method according to claim 8, wherein the measurement signal is detected by capturing and analyzing a series of images representing motion of the probe in the forward direction and the reverse direction.

15. A tonometer comprising:
a probe;
a conductive drive coil in which the probe is received;
a controller configured to momentarily energize the coil to propel the probe toward a cornea of an eye of a test subject;
a conductive measurement coil through which the probe moves;
wherein the controller is further configured to measure a current induced in the measurement coil by the moving probe and provide a measurement signal representing velocity of the probe as a function of time, and wherein the drive coil is energized such that a magnitude of the velocity of the probe is not kept constant after the probe is rebounded from the cornea; and
signal processing logic configured to calculate a first derivative of the measurement signal at a moment in time when velocity of the probe is zero due to contact of the probe with the cornea and correlate the first derivative to an intra-ocular pressure value.

16. The tonometer according to claim 15, wherein the drive coil is the measurement coil.

17. The tonometer according to claim 15, wherein the drive coil and the measurement coil are different coils.

18. A tonometry method comprising:
propelling a probe toward a cornea of an eye of a test subject such that a magnitude of the velocity of the probe is not kept constant after the probe is rebounded from the cornea;
detecting a measurement signal representing velocity of the probe as a function of time; and
calculating a first derivative of the measurement signal at a moment in time when velocity of the probe is zero due to contact of the probe with the cornea; and
correlating the first derivative to an intra-ocular pressure value.

19. The ophthalmic measurement method according to claim 18, wherein the measurement signal is detected using a measurement coil through which the probe moves, whereby the moving probe induces a current in the measurement coil.

20. The ophthalmic measurement method according to claim 18, wherein the measurement signal is detected by capturing and analyzing a series of images representing motion of the probe in the forward direction and the reverse direction.

* * * * *